United States Patent [19]

Kim

[11] Patent Number: 5,908,934

[45] Date of Patent: Jun. 1, 1999

[54] PROCESS FOR THE PREPARATION OF CHIRAL KETONE INTERMEDIATES USEFUL FOR THE PREPARATION OF FLAVOPIRIDOL AND ANALOGS

[75] Inventor: Kyoung Soon Kim, Lawrenceville, N.J.

[73] Assignee: Bristol-Myers Squibb Company, Princeton, N.J.

[21] Appl. No.: 08/927,609

[22] Filed: Sep. 12, 1997

Related U.S. Application Data

[60] Provisional application No. 60/026,748, Sep. 26, 1996.
[51] Int. Cl.$^6$ .................................................. C07D 211/74
[52] U.S. Cl. ......................... 546/216; 546/219; 546/220; 546/221; 546/222; 546/186; 546/194; 546/208; 546/210; 546/213; 546/214
[58] Field of Search .................................. 546/216, 219, 546/220, 221, 222

[56] References Cited

U.S. PATENT DOCUMENTS

| | | | |
|---|---|---|---|
| 4,900,727 | 2/1990 | Kattige et al. | 514/212 |
| 5,733,920 | 3/1998 | Mansuri et al. | 514/337 |

OTHER PUBLICATIONS

Baylet et al., "Resolution of Racemates by Diastereomeric Salt Formation," Chirality in Industry, pp. 69–77, 1992.
Jacques et al., "Enantiomers, Racemates, and Resolutions," pp. 380–383, 1981.
Morrison, "Organic Chemistry," Chapter 4, pp. 163–166, 1979.

*Primary Examiner*—Mukund J. Shah
*Assistant Examiner*—Ann M. Kessinger
*Attorney, Agent, or Firm*—Frank P. Hoffman

[57] ABSTRACT

A process for the preparation of compounds of formula I

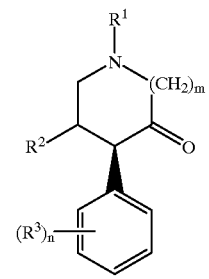

where $R^1$, $R^2$, $R^3$, m, n and q are as defined herein; which comprises the steps of (a) reacting a compound of formula III

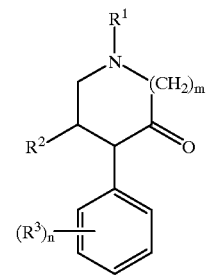

with a chiral acid in an organic solvent to form a salt of a compound of formula I and (b) treating the salt of a compound of formula I with an aqueous base to obtain the compounds of formula I. Compounds of formula I are intermediates useful in the preparation of protein kinase inhibitors.

21 Claims, No Drawings

PROCESS FOR THE PREPARATION OF CHIRAL KETONE INTERMEDIATES USEFUL FOR THE PREPARATION OF FLAVOPIRIDOL AND ANALOGS

The application claims benefit of Provisional application 60/026,748 filed Sep. 26, 1996.

BRIEF DESCRIPTION OF THE INVENTION

The present invention is directed to a process for preparing chiral compounds of the formula I

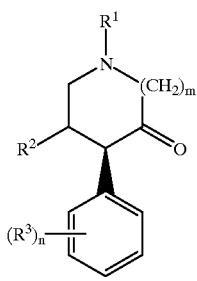

The compounds of formula I are intermediates for the preparation of protein kinase inhibitors which are useful in the treatment of proliferative diseases, for example, cancer, inflammation and arthritis. Compounds of the formula I may be used to prepare, for example, flavopiridol and analogs of the formula II

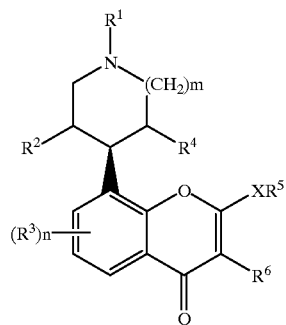

and pharmaceutically acceptable salts thereof. Compounds of the formula II are disclosed in U.S. Ser. No. 60/017,529, filed May 10, 1996, which is incorporated by reference herein. As used in formula I, II, and throughout the specification, the symbols have the following meanings:

X is a single bond, oxygen or sulfur;

$R^1$ is hydrogen, alkyl, aryl, arylalkyl, cycloalkyl, —($CH_2$)q—$NR^7R^8$, alkylcarbonyl, arylcarbonyl, arylalkylcarbonyl, alkyloxycarbonyl, arylalkyloxycarbonyl or aryloxycarbonyl;

$R^2$ is hydrogen, alkyl, arylalkyl, aryl, cycloalkyl, hydroxy, alkoxy, arylalkoxy, aryloxy, alkylcarbonyloxy, arylalkylcarbonyloxy, arylcarbonyloxy, carboxy, alkyloxycarbonyl, arylalkoxycarbonyl, aryloxycarbonyl, amino, —$NR^7R^8$, thiol, alkylthio, arylalkylthio or arylthio;

$R^3$ is hydrogen, alkyl, arylalkyl, aryl, cycloalkyl, hydroxy, alkoxy, arylalkoxy, aryloxy, alkylcarbonyloxy, arylalkylcarbonyloxy, arylcarbonyloxy, carboxy, alkyloxycarbonyl, arylalkoxycarbonyl, cyano, nitro, —$NR^7R^8$, halogen, alkylhalo, —CHO, alkylS(O)$_m$— or —OC(O)$NR^7R^8$;

$R^4$ is hydrogen, alkyl, arylalkyl, aryl, cycloalkyl, hydroxy, alkoxy, arylalkoxy, aryloxy, alkylcarbonyloxy, arylalkylcarbonyloxy, arylcarbonyloxy, carboxy, alkyloxycarbonyl, arylalkoxycarbonyl, aryloxycarbonyl, amino, —$NR^7R^8$, thiol, alkylthio, arylalkylthio or arylthio;

$R^5$ is alkyl, cycloalkyl, aryl, arylalkyl, heterocycle or heterocycloalkyl;

$R^6$ is hydrogen, alkyl, aryl, arylalkyl, nitro, amino, —($CH_2$)$_n$—$NR^7R^8$, halogen, hydroxy, alkoxy, carboxy, heterocycle or alkyloxycarbonyl;

$R^7$ and $R^8$ are independently hydrogen, alkyl, aryl, arylalkyl, cycloalkyl, heterocycle or alkylcarbonyl; or $R^7$ and $R^8$ together with the nitrogen atom to which they are bonded can form a heterocycle;

m is an integer of 0 to 2;

n is an integer of 1 to 3; and q is an integer of 2 to 5.

DESCRIPTION OF THE INVENTION

The present invention provides for a process for preparing the chiral ketone intermediates of formula I.

Listed below are definitions of various terms used to describe the compounds of the instant invention. These definitions apply to the terms as they are used throughout the specification (unless they are otherwise limited in specific instances) either individually or as part of a larger group.

It should be noted that any heteroatom with unsatisfied valances is assumed to have the hydrogen atom to satisfy the valances.

The term "alkyl" or "alk" refers to optionally substituted, straight and branched chain saturated hydrocarbon groups having 1 to 12 carbon atoms. Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include but are not limited to one or more of the following groups: halo (such as $CCl_3$ or $CF_3$), alkoxy, alkylthio, hydroxy, carboxy (—COOH), alkyloxycarbonyl, alkylcarbonyloxy, amino (—$NH_2$), —$NR^7R^8$, carbamoyl (—NHCOO— or —OCONH—), urea (—NHCONH—) or thiol (—SH).

The terms "alkoxy" or "alkylthio", as used herein, denote an alkyl group as described above bonded through an oxygen linkage (—O—) or a sulfur linkage (—S—), respectively.

The term "alkyloxycarbonyl", as used herein, denotes an alkoxy group bonded through a carbonyl group.

The term "alkylcarbonyl" refers to an alkyl group bonded through a carbonyl group.

The term "alkylcarbonyloxy", as used herein, denotes an alkylcarbonyl group which is bonded through an oxygen linkage.

The term "cycloalkyl" refers to optionally substituted, saturated cyclic hydrocarbon ring systems, preferably containing 1 to 3 rings and 3 to 7 carbons per ring. Exemplary unsubstituted such groups include cyclopropyl, cyclobutyl, cyclopentyl, cyclohexyl, etc. Exemplary substituents include one or more of the following groups: halogen, alkyl, alkoxy, alkyl hydroxy, amino, nitro, cyano, thiol and/or alkylthio.

The term "aryl" refers to monocyclic or bicyclic aromatic groups containing from 6 to 10 carbons in the ring portion, (such as phenyl or naphthyl), and may optionally be substituted with one or more groups selected from halogen, alkyl, alkoxy, alkylS(O)$_m$—, hydroxy, carboxy, carbamoyl, alkyloxycarbonyl, —CONR$^7$R$^8$, nitro, trifluoromethyl, amino and —NR$^7$R$^8$.

The term "heterocycle" or "heterocyclo" denotes optionally substituted, fully saturated or unsaturated, aromatic or non-aromatic cyclic groups having at least one heteroatom in at least one ring, preferably monocyclic or bicyclic groups having 5 or 6 atoms in each ring. The heterocyclo group may, for example, have 1 or 2 oxygen atoms and/or 1 or 2 sulfur atoms, and/or 1 to 4 nitrogen atoms in the ring. Each heterocyclo group may be bonded through any carbon or heteroatom of the ring system. Exemplary heterocyclo groups include the following: thienyl, furyl, pyrrolyl, pyridyl, imidazolyl, pyrrolidinyl, piperidinyl, azepinyl, indolyl, isoindolyl, quinolinyl, isoquinolinyl, benzothiazolyl, benzoxazolyl, benzimidazolyl, benzoxadiazolyl, benzofurazanyl and tetrahydropyranyl. Exemplary substituents include one or more of the following: halo, alkyl, alkoxy, hydroxy, cycloalkyl, hydroxy, nitro, cyano, amino, alkylS(O)$_m$— or thiol.

The term "halogen" or "halo" refers to chlorine, bromine, fluorine or iodine.

Compounds of the formula I are prepared by reacting compounds of formula III

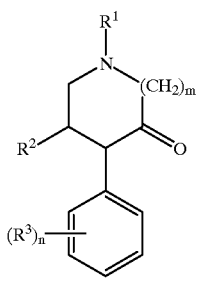

with a chiral acid such as D tartaric acid and its derivative or hydrate, mandelic acid and derivatives thereof, malic acid and its derivatives etc. in an organic solvent such as an alcohol or other halogenated solvent to form a salt of a compound of formula I.

The salt of the compound of formula I is then treated with an aqueous base such as aqueous sodium hydroxide to remove the chiral acid and obtain the desired chiral base of formula I.

Compounds of formula III are commercially available or may be prepared by methods known to one of ordinary skill in the art.

All compounds of formula I may be prepared by the procedures described herein or by modification of the procedures described herein.

The preferred method comprises the use of the chiral acid, dibenzoyl D tartaric acid.

The advantages of the method of this invention include the high yield generation of the desired enantiomer from the racemic mixture. This process converts the opposite enantiomer in the racemic mixture to the desired enantiomer via in situ epimerization.

The preferred compounds of formula I are those where:
R$^1$ is alkyl;
R$^2$ is hydrogen;
R$^3$ is alkoxy; and
n is the integer 3.

The compounds of formula II, including flavopiridol (which is the title compound of Example 2), have pharmacological properties; in particular, the compounds of formula II are inhibitors of protein kinases such as the cyclin dependent kinases (cdks), for example, cdc2 (cdk1), cdk2, and cdk4. The compounds of formula II are therefore expected to be useful in the therapy of proliferative diseases such as cancer, inflammation, and arthritis (Jorg Czech et al., "Antitumoral Activity of Flavone L 86-8275", *International Journal of Oncology* 6, 31–36 (1995); Gurmeet Kaur et al., "Growth Inhibition With Reversible Cell Cycle Arrest of Carcinoma Cells by Flavone L86-8275", *Journal of the National Cancer Institute*, 84, No. 22, 1736–1740 (1992); which are incorporated by reference herein).

More specifically, the compounds of formula II are useful in the treatment of a variety of cancers, including (but not limited to) the following:
carcinoma, including that of the bladder, breast, colon, kidney, liver, lung, ovary, pancreas, stomach, cervix, thyroid, prostate, and skin;
hematopoietic tumors of lymphoid lineage, including acute lymphocytic leukemia, B-cell lymphoma, and Burkett's lymphoma;
hematopoietic tumors of myeloid lineage, including acute and chronic myelogenous leukemias and promyelocytic leukemia;
tumors of mesenchymal origin, including fibrosarcoma and rhabdomyosarcoma; and
other tumors, including melanoma, seminoma, teratocarcinoma, osteosarcoma, neuroblastoma and glioma.

Due to the key role of cdks in the regulation of cellular proliferation in general, inhibitors could act as reversible cytostatic agents which may be useful in the treatment of any disease process which features abnormal cellular proliferation, e.g., neuro-fibromatosis, atherosclerosis, pulmonary fibrosis, arthritis, psoriasis, glomerulonephritis, restenosis following angioplasty or vascular surgery, hypertrophic scar formation, and endotoxic shock.

Compounds of formula II may also be useful in the treatment of Alzheimer's disease, as suggested by the recent finding that cdk5 is involved in the phosphorylation of tau protein (*J. Biochem*, 117, 741–749 (1995)).

Compounds of formula II may also act as inhibitors of other protein kinases, e.g., protein kinase C, her2, rafl, MEK1, MAP kinase, EGF receptor, PDGF receptor, IGF receptor, PI3 kinase, wee1 kinase, Src, Ab1 and thus be effective in the treatment of diseases associated with other protein kinases.

The compounds of formula II may also be useful in combination with known anti-cancer, cytostatic, and cytotoxic agents. If formulated as a fixed dose, such combination products employ the compounds of this invention within the dosage range described below and the other pharmaceutically active agent within its approved dosage range. For example, the cdc2 inhibitor olomucine has been found to act synergistically with known cytotoxic agents in inducing apoptosis (*J. Cell Sci.*, 108, 2897 (1995)). Compounds of formula II may be used sequentially with known anticancer or cytotoxic agents when a combination formulation is inappropriate.

The pharmacological properties of the compounds formula II may be confirmed by a number of pharmacological assays. The exemplified pharmacological assays which follow have been carried out with the compounds of formula II. The compound of example 2 exhibited cdc2/cyclin B1 kinase activity with $IC_{50}$ values less than 10 μM. The compound of example 2 exhibited cdk2/cyclin E kinase activity with $IC_{50}$ values less than 20 μM. The compound of example 2 exhibited cdk4/cyclin D1 kinase activity with $IC_{50}$ values less than 100 μM.

cdc2/cyclin B1 Kinase Assay cdc2/cyclin B1 kinase activity was determined by monitoring the incorporation of $^{32}P$ into histone HI. The reaction consisted of 50 ng baculovirus expressed GST-cdc2, 75 ng baculovirus expressed GST-cyclin B1, 1 μg histone HI (Boehringer Mannheim), 0.2 μCi of $^{32}P$ γ-ATP and 25 μM ATP in kinase buffer (50 mM Tris, pH 8.0, 10 mM $MgCl_2$, 1 mM EGTA, 0.5 mM DTT). The reaction was incubated at 30° C. for 30 minutes and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter (Marshak, D. R., Vanderberg, M. T., Bae, Y. S., Yu, I. J., J. of *Cellular Biochemistry*, 45, 391–400 (1991), incorporated by reference herein).

cdk2/cyclin E Kinase Assay cdk2/cyclin E kinase activity was determined by monitoring the incorporation of $^{32}P$ into the retinoblastoma protein. The reaction consisted of 2.5 ng baculovirus expressed GST-cdk2/cyclin E, 500 ng bacterially produced GST-retinoblastoma protein (aa 776–928), 0.2 μCi $^{32}P$ γ-ATP and 25 μM ATP in kinase buffer (50 mM Hepes, pH 8.0, 10 mM $MgCl_2$, 5 mM EGTA, 2 mM DTT). The reaction was incubated at 30° C. for 30 minutes and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter.

cdk4/cyclin D1 Kinase Assay cdk4/cyclin D1 kinase activity was determined by monitoring the incorporation of $^{32}P$ into the retinoblastoma protein. The reaction consisted of 165 ng baculovirus expressed GST-cdk4, 282 ng bacterially expressed S-tag cyclin D1, 500 ng bacterially produced GST-retinoblastoma protein (aa 776–928), 0.2 μCi $^{32}P$ γ-ATP and 25 μM ATP in kinase buffer (50 mM Hepes, pH 8.0, 10 mM $MgCl_2$, 5 mM EGTA, 2 mM DTT). The reaction was incubated at 30° C. for 1 hour and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter (Matsushime, H., Ewen, M. E., Strom, D. K., Kato, J-Y., Hanks, S. K., Roussel, M. F., Sherr, C. J. (1992) *Cell*, 71, 323–334, incorporated by reference herein).

The following examples and preparations describe the manner and process of making and using the invention and are illustrative rather than limiting. It should be understood that there may be other embodiments which fall within the spirit and scope of the invention as defined by the claims appended hereto.

EXAMPLE 1

(R)-1-Methyl-4-(2,4,6-trimethyoxyphenyl)-3-piperidinone

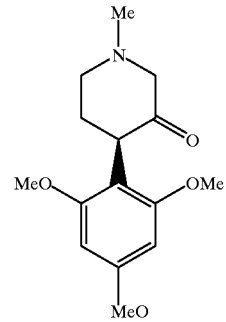

A mixture of (±)-1-methyl-4-(2,4,6-trimethoxyphenyl)-3-piperidinone (1.60 g, 5.73 mmoles) and dibenzoyl-D-tartaric acid (2.28 g, 315 mmol) in 10 mL of methanol was heated at reflux temperature under argon atmosphere and it was cooled to room temperature. After stirring overnight at room temperature the precipitated solid was filtered, washed with a small amount of methanol to obtain the first crop of (R)-1-methyl-4-(2,4,6-trimethoxyphenyl)-3-piperidinone dibenzoyl-D-tartaric acid salt (2.65 g). The filtrate solution was concentrated to a volume of ca 6 mL and was stirred at ambient temperature for one day. The second crop of the chiral salt (0.24 g) was obtained by filtering the solid and washed it with a small amount of methanol.

The combined solid salt (2.89 g) was dissolved in a mixture of $CH_2Cl_2$ (40 mL) and aq. NaOH solution (12 mL of 0.5 NaOH), the organic solution was taken, washed with brine, dried over $MgSO_4$ and concentrated under reduced pressure to obtain (R)-1-methyl-4-(2,4,6-trimethoxyphenyl)-3-piperidinone (1.216 g, 76% yield) as a white solid, mp 131–133° C. $[\alpha]_D$=+31° C. (MeOH, c 1.0). Chiral purity was determined by HPLC on OD Chiracel column (250×4.6 MM) eluting with 30% iso-propanol in hexane containing 0.1% triethylamine (flow rate: 1.0 muminute) at 254 nm.

$^1H$ NMR ($CDCl_3$) δ 6.28 (s, 2H), 4.01 (m, 1H), 3.92 (s, 3H), 3.88 (s, 6H), 3.58 (m, 1H), 3.13 (m, 1 H), 2.97 (m, 1 H), 2.61 (m, 1 H), 2.51 (s, 3H), 2,48 (m, 1H), 2.12 (m, 1H) ppm;

$^{13}C$ NMR ($CDCl_3$) δ 207.0, 151.5, 159.7, 109.7, 92.3, 67.7, 56.9, 56.4, 55.7, 47.2, 44.6, 30.5 ppm.

EXAMPLE 2

(3S-cis)-2-(2-Chlorophenyl)-8-(3-hydroxy-1-methyl-4-piperidinyl)-5,7-dihydroxy-4H-1-benzopyran4-one

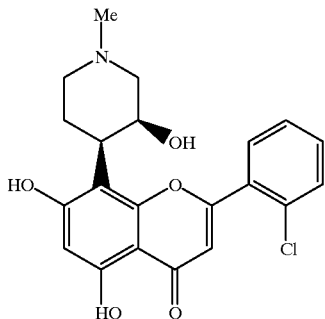

A. (3S-cis)-1-Methyl-4-(2,4,6-trimethyoxyphenyl)-3-piperidinol

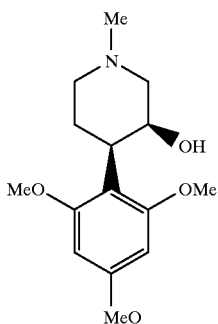

To a stirred solution of the title compound of Example 1 (25.0 g, 89.5 mmol) in CH$_2$Cl$_2$ (225 mL) at −76° C. (dry ice-acetone bath) was added dropwise a solution of diisobutylaluminum hydride (180 mmol, 180 mL of 1 M in CH$_2$Cl$_2$) under argon atmosphere with maintaining the reaction temperature below −65° C. The reaction mixture was stirred for 3.5 hours at −76° C. after the completion of addition. Trifluoroacetic acid (50 mL) was added dropwise to the reaction mixture at −76° C. After stirring the mixture for 15 minutes MeOH (250 mL) was added. It was warmed to room temperature and concentrated to obtain a solid residue, which was stirred with aqueous NaOH solution (2 N, 750 mL) for 15 minutes. The product was extracted with ethyl acetate (3×750 mL), the combined ethyl acetate solution was washed with brine, dried over Na$_2$SO$_4$ and concentrated to give a gum (25.0 g, 99%). This material was dissolved in CH$_2$Cl$_2$ and purified by flash chromatography (SiO$_2$, EtOAc:MeOH:Et$_3$N/100:20:0.2) to afford a cis- and trans-alcohol mixture as a foam, 22.0 g. This isomeric mixture was dissolved in 30% isopropanol in hexanes and passed through a Chiracel AD column (50×50 mm, Daicel chem. Ind. Ltd) eluting with 30% isopropanol in hexanes containing 0.2% Et$_3$N to obtain the title compound as a pure cis-alcohol (14.1 g, 56%), mp 111–112° C. (lit. 1, 109–111° C.).

$^1$H NMR (CDCl$_3$) δ 6.13 (s, 2H), 3.82 (s, 1H), 3.27 (s, 9H), 3.32 (m, 1H), 3.00 (m, 2H), 2.30 (s, 3H), 2.10 (m, 3H), 1.40 (m, 1H) ppm;

$^{13}$C NMR (CDCl$_3$) δ 159.6, 159.2, 111.5, 91.5, 70.4, 62.6, 57.1, 55.8, 55.3, 46.4, 36.8, 24.3 ppm; [α]$_D$=−53.8° C. (MeOH, c 1.0) (lit. 1, −54.13° C.).

B. (3S-cis)-4-(3-Acetyl-2-hydroxy-4,6-dimethyoxyphenyl)-1-methyl-3-piperidinol

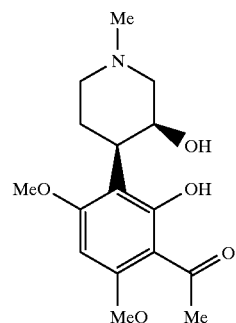

A solution of the title A compound (13.8 g, 49 mmol) in CH$_2$Cl$_2$ (250 mL) at 0° C. was added BF$_3$ etherate (50 mL) followed by acetic anhydride (40 mL). The resulting mixture was stirred at room temperature overnight and concentrated to remove the CH$_2$Cl$_2$. The residue was cooled in an ice bath and quenched with MeOH (300 mL). The mixture was stirred at room temperature for 15 minutes and concentrated in vacuo. The residue was dissolved in MeOH (300 mL) and stirred with 20% aqueous KOH solution (200 mL) for 48 hours. It was concentrated to remove the methanol and the residue was adjusted to pH 9.5 with 4 N hydrochloric acid. The product was extracted with CH$_2$Cl$_2$ (5×100 mL) and the combined CH$_2$Cl$_2$ extracts were dried over Na$_2$SO$_4$ and concentrated to afford a solid. The solid obtained was purified by flash chromatography (SiO$_2$; EtOAc:MeOH:Et$_3$N/100:15:0.2) to obtain a solid product which was triturated with diisopropyl ether (150 mL) to give the title compound (12.5 g, 82.6%) as a light yellow solid, mp 182° C. (lit. 1, 184–186° C.).

$^1$H NMR (CDCl$_3$) δ 6.11 (s, 1H), 4.03 (s, 3H), 4.01 (s, 3H), 4.0 (s, 1H), 3.50 (m, 1H), 3.16 (m, 3H), 2.73 (s, 3H), 2.46 (s,3H). 2.36 (m, 1H), 2.22 (m, 1 H), 1.56 (m, 1H) ppm;

$^{13}$C NMR (CDCl$_3$) δ 203.3, 264.0,163.7, 161.7, 109.9, 105.6, 86.1, 69.8, 62.2, 56.6, 55.2, 55.0, 46.0, 36.4, 32.8, 23.7 ppm; [α]$_D$=−34.5° C. (MeOH, c 1.0) (lit., −32.65° C.).

C. (3S-cis)-2-(2-Chlorophenyl)-8-(3-hydroxy-1-methyl4-piperidinyl)-5,7-dimethyoxy-4H-1-benzopyran-4-one

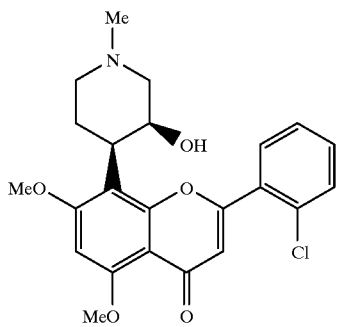

To a solution of methyl 2-chlorobenzoate (19.0 g, 111.6 mmol) and NaH (4.7 g, 95%, 186.0 mmol) in DMF (20 mL) at 0° C. was added a solution of the title B compound (11.5 g, 37.2 mmol) in DMF (100 mL) with stirring. After the completion of addition the mixture was stirred at room temperature for 4 hours. The mixture was poured onto ice and the resulting solution was adjusted to pH 10 with 1 N hydrochloric acid. The product was extracted with CH$_2$Cl$_2$ (4×150 mL). The CH$_2$Cl$_2$ extract was concentrated and the residue was diluted with CHCl$_3$ (100 mL). The solution was saturated with gaseous hydrogen chloride at room temperature and stirred for 1 hour. The solution was made alkaline with aqueous Na$_2$CO$_3$ solution and the organic layer was separated. The aqueous layer was extracted with CH$_2$Cl$_2$ (3×150 mL). The combined organic solution was dried over Na$_2$SO$_4$ and concentrated in vacuo. The residue was purified by flash chromatography (SiO$_2$; EtOAc:MeOH:Et$_3$N/ 100:15:0.2) to afford the title compound (9.1 g, 57%) as a foam.

$^1$H NMR (CDCl$_3$) δ 7.74–7.52 (m, 4H), 6.60 (s, 1H), 6.59 (s, 1H), 4.14 (s, 3 H), 4.11 (s, 3H), 4.10 (s, 1H), 3.65 (m, 1H), 3.55 (m, 1H), 3.18 (m, 3H), 2.50 (s, 3H), 2.40 (m, 1H), 2.38 (m, 1H), 1.73 (m, 1H) ppm;

$^{13}$C NMR (CDCl$_3$) δ 178.2, 163.1, 160.7, 160.4, 157.6, 133.1, 132.2, 131.3, 127.8, 114.4, 111.1, 93.1, 70.5, 63.0, 57.3, 56.9, 56.6, 46.7, 38.4, 24.7, 14.7 ppm; [α]$_D$=–60.5° C. (MeOH, c 1.0).

D. (3S-cis)-2-(2-Chlorophenyl)-8-(3-hydroxy-1-methyl-4-piperidinyl)-5,7-dihydroxy-4H-1-benzopyran-4-one

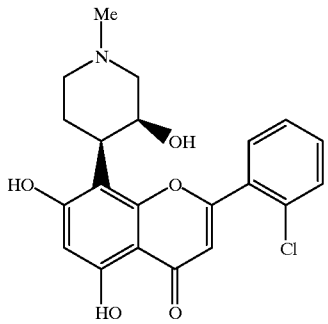

To a solution of the title C compound (9.0 g, 20.9 mmol) in 1,2-dichloroethane (120 mL) at 0° C. was added a solution of BBr$_3$ (42.0 g, 168 mmol) in 1,2-dichloroethane (80 mL) with a vigorous stirring. The resulting mixture was stirred at 80° C. for 8 hours and 90° C. for 5 hours. It was cooled to room temperature and poured onto ice. The mixture was made alkaline with aqueous Na$_2$CO$_3$ solution to pH 9–10 and the organic layer was taken. The heterogeneous aqueous layer containing desired product was washed with CH$_2$Cl$_2$ (6×150 mL). The combined organic solution was dried over Na$_2$SO$_4$ and concentrated. The residue was triturated with CH$_2$Cl$_2$—MeOH (100:5) to obtain a yellow solid product. This solid was stirred in MeOH (100 mL) containing 1 N hydrochloric acid (20 mL) at room temperature until it became a clear solution. It was concentrated in vacuo and the residue was stirred in MeOH (20 mL) at reflux temperature for 10 minutes. It was cooled to room temperature and ethyl ether (50 mL) was added to the mixture. The precipitated solid was filtered, washed with ethyl ether three times and dried to afford a solid, 6.7 g which contained the title compound methanol. This solid was dissolved in water (100 mL) and lyophilized to give the title compound (6.4 g, 67%) as a pale yellow solid, mp 195–197° C. (lit. 1, 190–194° C.).

$^1$H NMR (CD$_3$OD) δ 7.76 (dd, J=2.3 and 7.2 Hz, 1H), 7.60 (m, 3H), 6.48 (s, 1 H), 6.33 (s, 1H), 4.27 (s, 1H), 3.71 (m, 1H), 3.54–3.32 (m, 3H), 3.15 (m, 2 H), 2.87 (s, 3H), 1.87 ( m, 1H) ppm;

$^{13}$C NMR (CD$_3$OD) δ 1,84.0, 164.9, 164.6, 162.3, 157.7, 133.6, 132.9, 132.4, 131.9, 128.9, 111.8, 107.2, 106.0, 101.2, 68.2, 61.7, 56.7, 44.2, 37.3, 23.4; MS (ESI) m/e 402 (M+H)$^+$, 400 (M–H)$^-$. [α]$_D$=–3.3° C. (MeOH, c 1.0) ((lit. 1, –3.4° C.).

What is claimed is:

1. A process for the preparation of compounds of formula

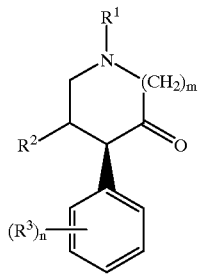

where

R$^1$ is hydrogen, alkyl, aryl, arylalkyl, cycloalkyl, —(CH$_2$)q—NR$^7$R$^8$, alkylcarbonyl, arylcarbonyl, arylalkylcarbonyl, alkyloxycarbonyl, arylalkyloxycarbonyl or aryloxycarbonyl;

R$^2$ is hydrogen, alkyl, arylalkyl, aryl, cycloalkyl, hydroxy, alkoxy, arylalkoxy, aryloxy, alkylcarbonyloxy, arylalkylcarbonyloxy, arylcarbonyloxy, carboxy, alkyloxycarbonyl, arylalkoxycarbonyl, aryloxycarbonyl, amino, —NR$^7$R$^8$, thiol, alkylthio, arylalkylthio or arylthio;

R$^3$ is hydrogen, alkyl, arylalkyl, aryl, cycloalkyl, hydroxy, alkoxy, arylalkoxy, aryloxy, alkylcarbonyloxy, arylalkylcarbonyloxy, arylcarbonyloxy, carboxy, alkyloxycarbonyl, arylalkoxycarbonyl, cyano, nitro, —NR$^7$R$^8$, halogen, alkylhalo, —CHO, alkylS(O)$_m$— or —OC(O)NR$^7$R$^8$;

R$^7$ and R$^8$ are independently hydrogen, alkyl, aryl, arylalkyl, cycloalkyl, 5 or 6 membered heterocycle or alkylcarbonyl; or R$^7$ and R$^8$ tegether with the nitrogen atom to which they are bonded can form a 5 or 6 membered heterocycle;

m is 1 n is an integer of 1 to 3; and q is an integer of 2 to 5;

which comprises the steps of (a)reacting a compound of formula III

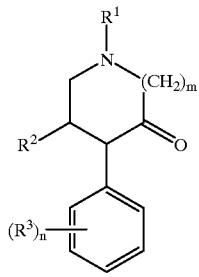

with a chiral acid in an organic solvent to form a salt of a compound of formula I and (b) treating the salt of a compound of formula I with an aqueous base to obtain the compounds of formula I.

2. The process as recited in claim 1 wherein the chiral acid is D tartaric acid, its derivative or hydrate.

3. The process as recited in claim 1 wherein the chiral acid is mandelic acid or derivatives thereof.

4. The process as recited in claim 1 wherein the chiral acid is malic acid or its derivatives.

5. The process as recited in claim 1 wherein the organic solvent is alcohol or a halogenated solvent.

6. The process as recited in claim 2 wherein the organic solvent is alcohol or a halogenated solvent.

7. The process as recited in claim 3 wherein the organic solvent is alcohol or a halogenated solvent.

8. The process as recited in claim 4 wherein the organic solvent is alcohol or a halogenated solvent.

9. The process as recited in claim 1 wherein the aqueous base is aqueous sodium hydroxide.

10. The process as recited in claim 2 wherein the aqueous base is aqueous sodium hydroxide.

11. The process as recited in claim 3 wherein the aqueous base is aqueous sodium hydroxide.

12. The process as recited in claim 4 wherein the aqueous base is aqueous sodium hydroxide.

13. The process as recited in claim 5 wherein the aqueous base is aqueous sodium hydroxide.

14. The process as recited in claim 6 wherein the aqueous base is aqueous sodium hydroxide.

15. The process as recited in claim 7 wherein the aqueous base is aqueous sodium hydroxide.

16. The process as recited in claim 8 wherein the aqueous base is aqueous sodium hydroxide.

17. The process as recited in claim 1 wherein $R^1$ is alkyl;

$R^2$ is hydrogen;

$R^3$ is alkoxy; and n is the integer 3.

18. The process as recited in claim 17 wherein the chiral acid is D tartaric acid, its derivative or hydrate, mandelic acid or derivatives thereof or malic acid or its derivatives.

19. The process as recited in claim 18 wherein the chiral acid is dibenzoyl D tartaric acid.

20. The process as recited in claim 18 wherein the organic solvent is alcohol or a halogenated solvent.

21. The process as recited in claim 20 wherein the aqueous base is aqueous sodium hydroxide.

* * * * *